(12) United States Patent
Greenberg et al.

(10) Patent No.: US 7,611,529 B2
(45) Date of Patent: Nov. 3, 2009

(54) THORACIC INTRODUCER

(75) Inventors: Roy K. Greenberg, Bratenahl, OH (US); David Ernest Hartley, Subiaco (AU); Erik Edelboe Rasmussen, Slagelse (DK)

(73) Assignees: Cook Incorporated, Bloomington, IN (US); William Cook Europe ApS, Bjaeverskov (DK); William A. Cook Australia Pty. Ltd., Brisbane (AU)

( * ) Notice: Subject to any disclaimer, the term of this patent is extended or adjusted under 35 U.S.C. 154(b) by 454 days.

(21) Appl. No.: 10/609,842

(22) Filed: Jun. 30, 2003

(65) Prior Publication Data

US 2004/0106974 A1   Jun. 3, 2004

Related U.S. Application Data

(60) Provisional application No. 60/392,599, filed on Jun. 28, 2002.

(51) Int. Cl.
  *A61F 2/06* (2006.01)
(52) U.S. Cl. .................................. 623/1.11; 606/108
(58) Field of Classification Search ............... 623/1.15, 623/1.22, 1.12, 1.23, 1.11; 606/108, 159
  See application file for complete search history.

(56) References Cited

U.S. PATENT DOCUMENTS

| | | | |
|---|---|---|---|
| 2,907,321 A * | 10/1959 | Rubens | 600/104 |
| 4,665,918 A * | 5/1987 | Garza et al. | 606/108 |
| 5,147,334 A | 9/1992 | Moss | |
| 5,387,235 A | 2/1995 | Chuter | |
| 5,569,204 A * | 10/1996 | Cramer | 604/164.1 |
| 5,720,776 A | 2/1998 | Chuter et al. | |
| 5,776,142 A * | 7/1998 | Gunderson | 623/1.11 |
| 6,183,481 B1 * | 2/2001 | Lee et al. | 606/108 |
| 6,206,931 B1 | 3/2001 | Cook et al. | |
| 6,346,118 B1 | 2/2002 | Baker et al. | |
| 6,371,979 B1 * | 4/2002 | Beyar et al. | 623/1.12 |
| 6,699,274 B2 * | 3/2004 | Stinson | 623/1.12 |
| 6,939,370 B2 | 9/2005 | Hartley et al. | |
| 2003/0120332 A1 | 6/2003 | Hartley | |
| 2003/0233140 A1 | 12/2003 | Hartley et al. | |
| 2004/0054396 A1 | 3/2004 | Hartley et al. | |
| 2004/0073289 A1 | 4/2004 | Hartley | |
| 2004/0106978 A1 | 6/2004 | Greenberg et al. | |
| 2004/0181235 A1 * | 9/2004 | Daignault et al. | 606/108 |

FOREIGN PATENT DOCUMENTS

| | | |
|---|---|---|
| WO | 9853761 | 12/1998 |
| WO | 9929262 | 3/1999 |
| WO | 03034948 | 5/2003 |

* cited by examiner

*Primary Examiner*—Anhtuan T Nguyen
*Assistant Examiner*—Tuan V Nguyen
(74) *Attorney, Agent, or Firm*—Richard J. Godlewski

(57) ABSTRACT

A stent graft deployment apparatus (10) which has a deployment catheter (11) with a proximal end (5) to be introduced into a patient and a distal end (3) to remain outside a patient and at a proximal end thereof a region to contain a stent graft (21). A sheath (25) extends over and covers the stent graft and can be moved to expose the stent graft to enable deployment of the stent graft. A nose cone dilator (17) is positioned at the proximal end of the deployment catheter and can be curved. A capsule (40) provides a distal retention arrangement for the stent graft.

12 Claims, 3 Drawing Sheets

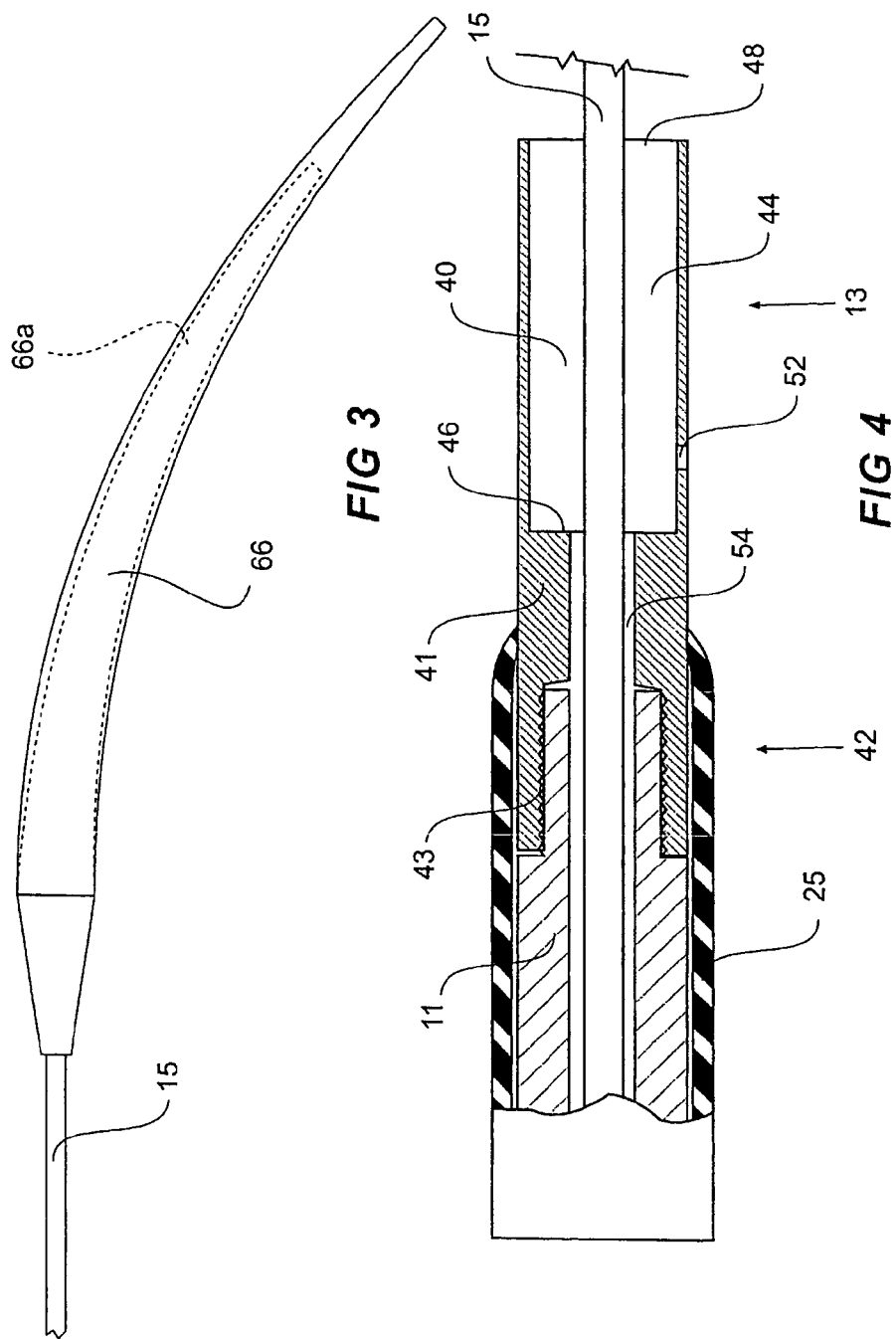

THORACIC INTRODUCER

CROSS-REFERENCE TO RELATED APPLICATION

This application claims priority of provisional application Ser. No. 60/392,599, filed Jun. 28, 2002.

TECHNICAL FIELD

This invention relates to the field of medical devices and more particularly to devices for introduction of vascular devices into the body of a human or animal.

BACKGROUND OF THE INVENTION

In recent years endovascular implantable devices have been developed for treatment of aortic aneurysm. These devices are delivered to the treatment site through the vascular system of the patient rather than by open surgery. The devices include a tubular or cylindrical framework or scaffolding of one or more stents to which is secured a tubular shape of graft material such as woven Dacron, polyester polytetrafluoroethylene or the like. The devices are initially reduced to a small diameter, placed into the leading or proximal end of a catheter delivery system whereafter the delivery system is inserted into the vascular system of the patient such as through a femoral incision. The leading end of the delivery system is maneuvered to the treatment site over a previously positioned guide wire. Through manipulation of a control system that extends to the proximal end of the catheter from the distal end of the system outside the patient the implantable device is then deployed by holding the device at its location and drawing a surrounding sheath. The stent graft or implantable device can then self expand or is expanded through the use of a balloon which is introduced with the stent graft introducible device. The stent graft becomes anchored into position to healthy wall tissue in the aorta such as by barbs whereafter the delivery system is then removed leaving the device in position for reversing an aneurysm in the aorta. All blood flow is channeled through the stent graft so that no blood flow enters the aneurysm thereafter, such that not only does the aneurysm no longer continue to grow and possibly rupture but the aneurysm actually begins to shrink and commonly disappears entirely.

For treatment of thoracic aortic aneurysms in particular it is necessary to introduce the implantable device high up in the aorta and in a region of the aorta which is curved and where there can be strong blood flow.

If an implantable device which is essentially a tube is deployed in the thoracic arch by first releasing the proximal end, that is the end nearer the heart, then blood flow could inflate the stent graft in the manner of a wind sock and there will be considerable pressure of blood flow to displace the implantable device from its intended position.

It is desirable therefore that a deployment device or deployment system is provided which enables release of the distal end of a stent graft or implantable device before the proximal end.

It is the object of this invention to provide a device which will overcome at least some of these problems or at least provide the physician with a useful alternative.

SUMMARY OF THE INVENTION

In one form therefore although this may not necessarily be the only or broadest form the invention is said to reside in a stent graft delivery system for a thoracic aorta stent graft comprising, a tubular central carrier having a distal end and a proximal end, a nose cone dilator positioned at the proximal end of the tubular carrier, a capsule having a passage way extending there in with the distal end closed and attached to the tubular carrier and an open air proximal end facing a nose cone dilator, the capsule being axially movable along the tubular carrier with respect to the nose cone dilator.

Preferably there is a longitudinal lumen through the tubular central carrier and a guide wire catheter extending through the longitudinal lumen for a guide wire and the nose cone dilator being attached to the guide wire catheter.

In one embodiment the tubular central carrier and nose cone dilator together are curved to provide a curved proximal end which can have a radius of curvature of from 70 to 150 millimetres. Alternatively just the nose cone dilator is curved.

The capsule provides a first retention arrangement on the tubular carrier for the distal end of a stent graft. Preferably the first retention arrangement includes an aperture extending through the capsule and a distal trigger wire extending along the tubular carrier and extendable through the aperture. Preferably the distal trigger wire extends through the longitudinal lumen.

There can be a second retention arrangement on the tubular carrier for the proximal end of the stent graft. The second retention arrangement can be distal of the nose cone dilator.

The nose cone dilator can have one or more apertures extending longitudinally therein and wherein the delivery system can include one or more proximal trigger wires extending longitudinally along said tubular carrier and independently extendable into said one or more apertures of said nose cone.

In an alternative form the invention is said to reside in a stent graft delivery system for a thoracic aorta stent graft comprising; a tubular central carrier having a distal end and a proximal end; a nose cone dilator at the proximal end of the tubular carrier; a first retention arrangement on the tubular carrier for the distal end of a stent graft; and the tubular carrier and the nose cone dilator having a curved proximal end.

In an alternative form the invention is said to reside in a stent graft delivery system for a thoracic aorta stent graft comprising; a tubular central carrier having a distal end and a proximal end; a nose cone dilator positioned at the proximal end of the tubular carrier; a capsule having a passageway extending therein with the distal closed end attached to the tubular carrier and an open proximal end facing the nose cone dilator; the capsule being axially moveable along the tubular carrier with respect to the nose cone dilator; and the tubular carrier and the nose cone dilator having a curved proximal end.

In an alternative form the invention is said to reside in a stent graft delivery system for a thoracic aorta stent graft comprising; a tubular central carrier having a distal end and a proximal end; a nose cone dilator positioned at the proximal end of the tubular carrier; a capsule having a passageway extending therein with the distal closed end attached to the tubular carrier and an open proximal end facing the nose cone dilator; the capsule being axially moveable along the tubular carrier with respect to the nose cone dilator; a longitudinal lumen through the tubular central carrier; a guide wire catheter extending through the longitudinal lumen, the nose cone dilator being attached to the guide wire catheter; and the tubular carrier and the nose cone dilator having a curved proximal end.

In an alternative form the invention is said to reside in a stent graft delivery system for a thoracic aorta stent graft comprising; a tubular central carrier having a distal end and a proximal end; a longitudinal lumen through the tubular central carrier; a guide wire catheter extending through the longitudinal lumen and extending proximally of the tubular central carrier the guide wire catheter having a proximal end and a distal end; the guide wire catheter being movable longitudinally and rotationally with respect to the tubular central carrier; a nose cone dilator being attached to proximal end of the guide wire catheter and extending proximally thereof; a capsule having a passageway extending therein with the distal closed end attached to the proximal end of the tubular carrier and an open proximal end facing the nose cone dilator, the capsule providing a distal retention arrangement for the stent graft; and the nose cone dilator having a curved proximal end.

Preferably there is a coaxial sheath over the tubular central carrier, the coaxial sheath being movable with respect to the tubular central carrier and extending to the nose cone dilator.

There can be a proximal retention arrangement on the guide wire catheter distal of the nose cone dilator for the proximal end of the stent graft.

In an alternative form the invention is said to reside in a stent graft deployment apparatus comprising; a deployment catheter having a proximal end adapted to be introduced into a patient and a distal end adapted to remain outside a patient, the catheter having at a proximal end thereof a region adapted in use to contain a stent graft; a sheath arrangement adapted in use to extend over and cover the region adapted to be moved with respect to the catheter to expose the region to thereby enable deployment of the stent graft; a nose cone dilator positioned at the proximal end of the deployment catheter; a distal retention arrangement for the stent graft at a distal end of the region and comprising a capsule having a passageway extending therein with a distal closed end and an open proximal end facing the nose cone dilator.

The proximal retention arrangement can include at least one proximal trigger wire with the trigger wire extending from the outside of the patient where it is retained by a trigger wire release mechanism on a handle at the distal end of the deployment catheter.

BRIEF DESCRIPTION OF THE DRAWING

In the drawings:

FIG. 3 shows one embodiment of nose cone dilator according to the invention; and FIG. 4 shows a part cross-sectional view of the capsule portion of a deployment device according to an embodiment of this invention.

DETAILED DESCRIPTION

Figure 1:
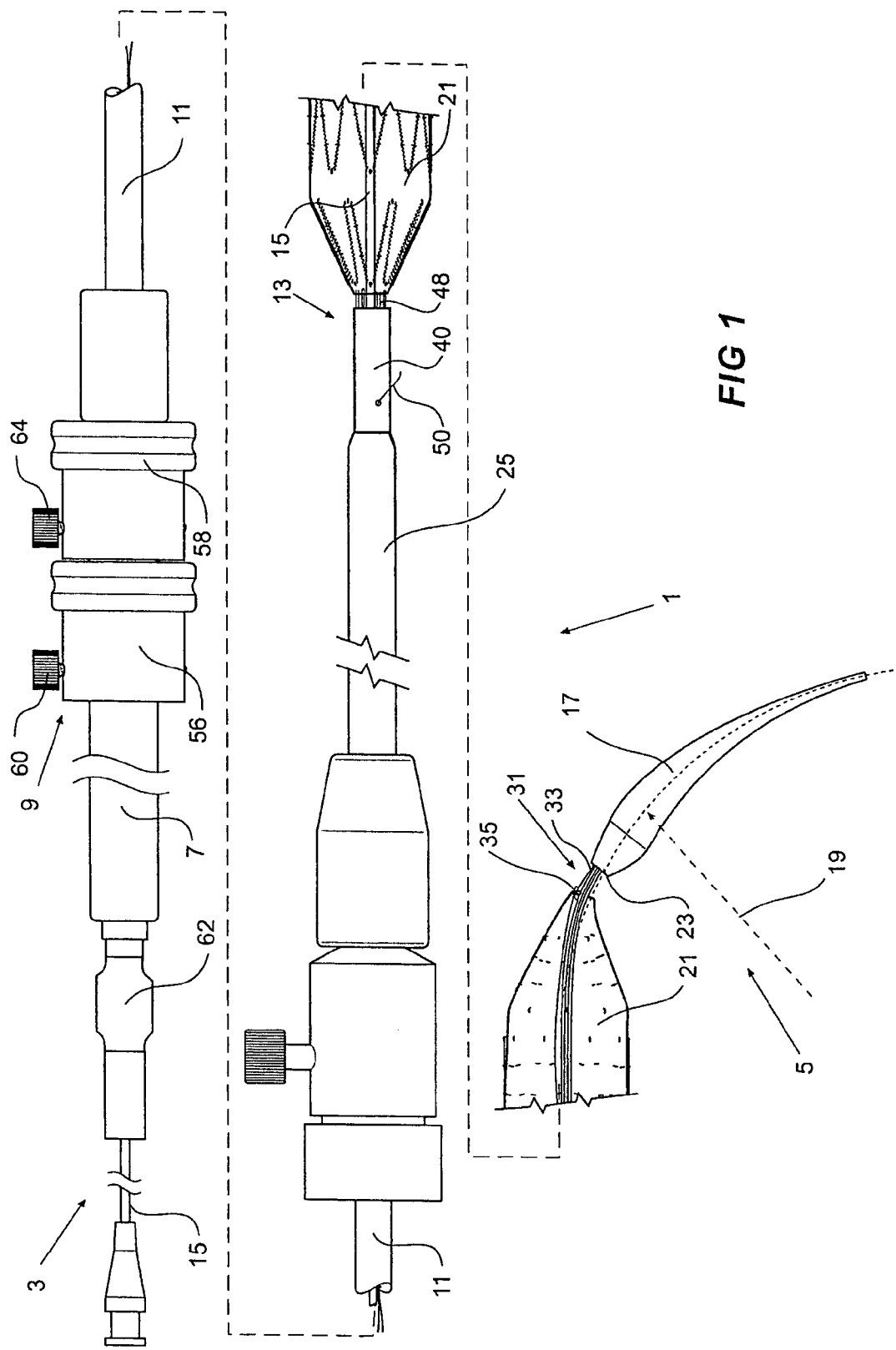
FIG. 1 shows a general view of a stent graft delivery system according to one embodiment of the present invention with a stent graft partially released.

U.S. Pat. No. 5,387,235 entitled "Expandable Transluminal Graft Prosthesis For Repair Of Aneurysm" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Barb and Expandable Transluminal Graft Prosthesis For Repair Of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

PCT Patent Publication No. WO 98/53761 entitled "A Prosthesis And A Method And Means Of Deploying A Prosthesis" discloses an introducer for a prosthesis which retains the prosthesis so that each end can be moved independently. These features and other features disclosed in PCT Patent Publication No. WO 98/53761 could be used with the present invention and the disclosure of PCT Patent Publication No. WO 98/53761 is herewith incorporated in its entirety into this specification.

PCT Patent Publication No. WO 99/29262 entitled "Endoluminal Aortic Stents" discloses a fenestrated prosthesis for placement where there are intersecting arteries. This feature and other features disclosed in PCT Patent Publication No. WO 99/29262 could be used with the present invention and the disclosure of PCT Patent Publication No. WO 99/29262 is herewith incorporated in its entirety into this specification.

PCT Patent Publication Number WO 03/034948 entitled "Prosthesis for Curved Lumens" discloses prostheses with arrangements for bending the prosthesis for placement into curved lumens. This feature and other features disclosed in PCT Patent Publication No. WO 03/034948 could be used with the present invention and the disclosure of PCT Patent Publication No. WO 03/034948 is herewith incorporated in its entirety into this specification.

U.S. Provisional Patent Application Ser. No. 60/392,682, filed Jun. 28, 2003, entitled "Trigger Wires" discloses release wire systems for the release of stent grafts retained on introducer devices. This feature and other features disclosed in U.S. Provisional Patent Application Ser. No. 60/392,682 could be used with the present invention and the disclosure of U.S. Provisional Patent Application Ser. No. 60/392,682 is herewith incorporated in its entirety into this specification.

U.S. Provisional Patent Application Ser. No. 60/392,667, filed Jun. 28, 2002, entitled "Thoracic Deployment Device" discloses introducer devices adapted for deployment of stent grafts particularly in the thoracic arch. This feature and other features disclosed in U.S. Provisional Patent Application Ser. No. 60/392,667 could be used with the present invention and the disclosure of U.S. Provisional Patent Application Ser. No. 60/392,667 is herewith incorporated in its entirety into this specification.

U.S. Provisional Patent Application Ser. No. 60/392,599, filed Jun. 28, 2002, entitled "Thoracic Aortic Aneurysm Stent Graft" discloses stent grafts that are useful in treating aortic aneurysms particularly in the thoracic arch. This feature and other features disclosed in U.S. Provisional Patent Application Ser. No. 60/392,599, could be used with the present invention and the disclosure of U.S. Provisional Patent Application Ser. No. 60/392,599, is herewith incorporated in its entirety into this specification.

U.S. Provisional Patent Application Ser. No. 60/391,737, filed Jun. 26, 2002, entitled "Stent-Graft Fastening Arrangement" discloses arrangements for fastening stents onto grafts particularly for exposed stents. This feature and other features disclosed in U.S. Provisional Patent Application Ser. No. 60/391,737 could be used with the present invention and the disclosure of U.S. Provisional Patent Application Ser. No. 60/391,737 is herewith incorporated in its entirety into this specification.

U.S. Provisional Patent Application No. 60/405,367, filed Aug. 23, 2002, entitled "Asymmetric Stent Graft Attachment" discloses retention arrangements for retaining onto and releasing prostheses from introducer devices. This feature and other features disclosed in U.S. Provisional Patent Application No. 60/405,367 could be used with the present invention and the disclosure of U.S. Provisional Patent Application No. 60/405,367 is herewith incorporated in its entirety into this specification.

U.S. patent application Ser. No. 10/322,862, filed Dec. 18, 2002 entitled "Stent Graft With Improved Adhesion" discloses arrangements on stent grafts for enhancing the adhesion of such stent grafts into walls of vessels in which they are deployed. This feature and other features disclosed in U.S. patent application Ser. No. 10/322,862 could be used with the present invention and the disclosure of U.S. patent application Ser. No. 10/322,862 is herewith incorporated in its entirety into this specification.

This then generally describes the invention but to assist with the understanding, reference will now be made to the accompanying drawings which show a preferred embodiment of the invention.

Figure 2:
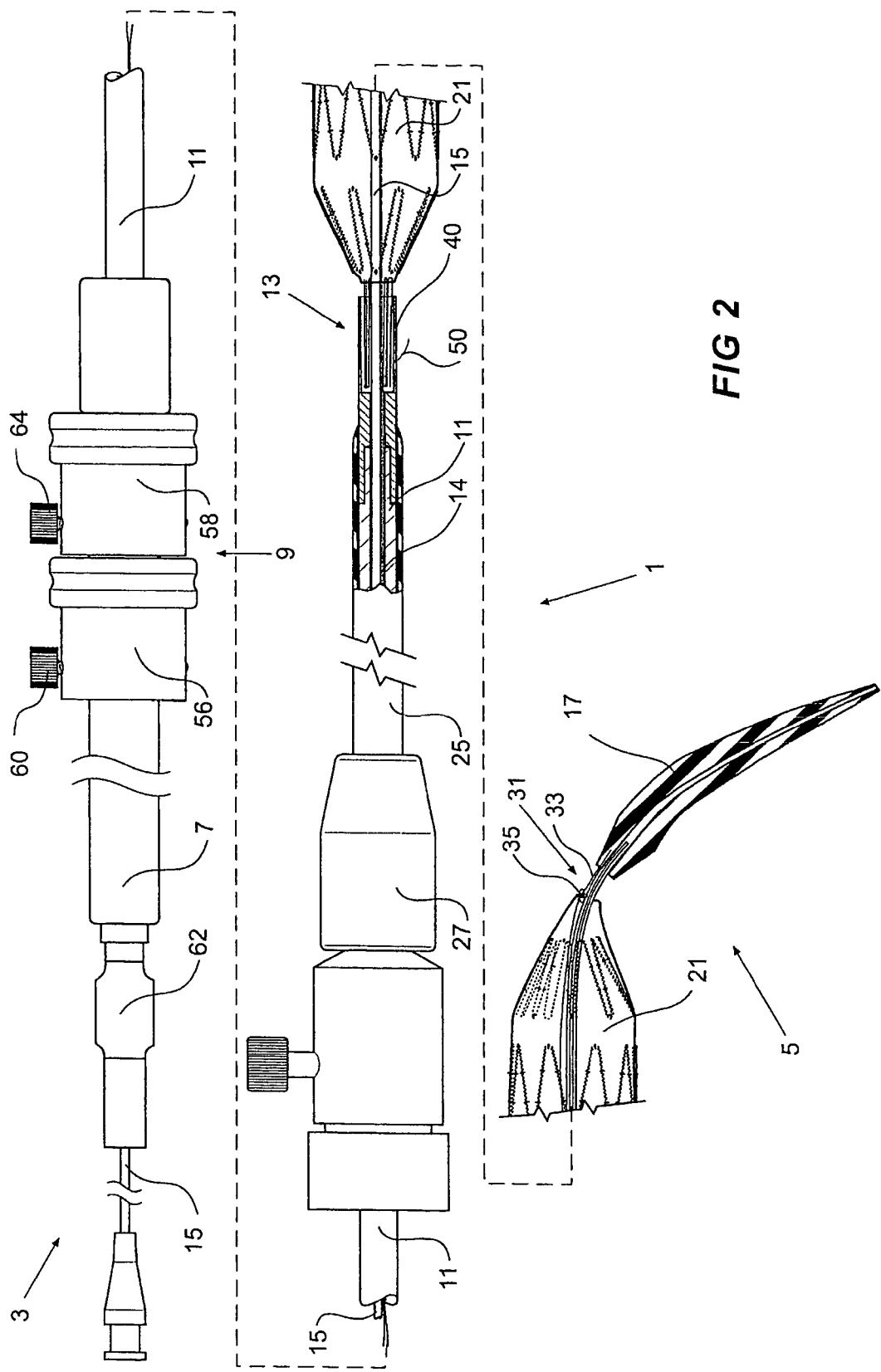
FIG. 2 shows a part cross-sectional view of the embodiment shown in FIG. 1.

Now looking more closely at FIGS. 1 and 2 it will be seen that a stent graft delivery system 1 according to the invention has a distal end 3 which in use is intended to remain outside a patient and a proximal end 5 which is introduced into the patient.

Towards the distal end there is a handle arrangement 7 which includes trigger wire release apparatus 9 as will be discussed later. The main body of the deployment device includes a tubular carrier 11 which extends from the handle 7 to a distal retention arrangement general shown as 13.

Within a longitudinal lumen 14 in the central carrier 11 extends a guide wire catheter 15. The guide wire catheter 15 extends out through the distal retention arrangement 13 and extends to a nose cone dilator 17 at the proximal end of the deployment device 1. The nose cone dilator 17 is curved and in the embodiment shown in FIG. 1 the guide wire catheter 15 is also curved towards its proximal end so that the proximal end 5 of the deployment device has a curve which may have a radius of curvature 19 of between 70 to 150 millimetres. This curvature enables the stent graft deployment device of the present invention to be introduced into the thoracic arch of a patient without excessive load being placed on the walls of the aorta.

A stent graft 21 is retained on the deployment device between the distal end 23 of the nose cone dilator 17 and the distal retention arrangement 13. A sleeve 25 fits over the tubular carrier 11 and by operation of a sleeve manipulator 27 the sleeve can be extended forward to extend to the nose cone dilator 17. By the use of the sleeve 25 the stent graft 21 can be held in a constrained position within the sleeve.

At the proximal end of the stent graft just distal of the distal end 23 of the nose cone dilator 17 a proximal retention arrangement 31 is provided.

The proximal retention arrangement 31 includes a trigger wire 33 which engages a knot 35 of suture material which is fastened to the trigger wire 33 and the guide wire catheter 15. When the trigger wire 33 is withdrawn as will be discussed later, the suture knot 25 is released and the proximal end of the stent graft can be released. The nose cone dilator 17 can have one or more apertures extending longitudinally, and the proximal trigger wire 33 can extend into one of these apertures.

The distal retention arrangement 13 as shown in detail in FIG. 4 includes a capsule 40 which is part of a capsule assembly 41 which is joined by a screw thread 43 to the proximal end 42 of the central carrier 11. The capsule 40 includes a passageway 44 within it with a distal closed end 46 and an open proximal end 48. The open proximal end 48 faces the nose cone dilator 17 and the guide wire catheter 15 passes through the center of passageway 44.

The stent graft 21 has a distally extending exposed stent 48 and this distally extending exposed stent 48 is received within the capsule 40 which holds it constrained during deployment. If the distally extending exposed stent 48 has barbs extending from its struts then the capsule keeps the barbs from prematurely engaging the walls of the vessel it is being deployed in and also prevents them from catching in the sleeve 25. A trigger wire 50 passes through aperture 52 in the side of the capsule, engages a loop of the exposed stent 48 within the capsule and then passes along the annular recess 54 between the guide wire catheter 15 and the tubular carrier 11 to the trigger wire release mechanism 9.

The trigger wire release mechanism 9 includes a distal release mechanism 56 and a proximal end release mechanism 58.

To release the stent graft after it has been placed in the desired position in the thoracic arch, the sleeve 25 is withdrawn by pulling back on the sleeve manipulator 27 while holding the handle 7 stationary. The distal release mechanism 56 on the handle 7 is then released by loosening the thumb screw 60 and completely withdrawing the distal release mechanism 56 which pulls out the trigger wire 50 from the capsule 40. Pin vice 62 which fixes the position of the guide wire catheter with aspect to the handle 7 and central carrier 11 is then loosened so that the guide wire catheter 15 can be held stationary which holds the nose cone dilator and hence the proximal retention arrangement 31 stationary while the handle is pulled back to remove the capsule 40 from the exposed stent 48 which releases the distal end of the stent graft.

Once the position of the proximal end of the stent graft 21 has been checked, the proximal release mechanism 58 can then be removed by release of the thumb screw 64 and complete removal of the proximal release mechanism 58 which pulls the guide wire 33 from the proximal end of the stent graft which releases the suture knot 35 which releases the proximal end of the stent graft.

The tubular central carrier 11 can then be advanced while holding the nose cone dilator 17 stationary so that the deployment device can be made more compact for withdrawal.

FIG. 3 shows an alternative embodiment of nose cone dilator. In this embodiment, the guide wire catheter 15 is substantially straight and the curved proximal end of the deployment device has a curvature only in the region of the nose cone dilator 66. The radius of curvature of this nose cone dilator may be in the range of 100 to 150 millimetres and it can have a length of from 80 mm as shown by 66a up to 100 mm as shown by 66.

Throughout this specification various indications have been given as to the scope of the invention but the invention is not limited to any one of these but may reside in two or more of these combined together. The examples are given for illustration only and not for limitation.

What is claimed is:

1. A thoracic stent graft delivery system for positioning a thoracic aorta stent graft into a thoracic aortic arch of a patient, the delivery system comprising;
   a tubular central carrier having a distal end and a proximal end;
   a longitudinal lumen through the tubular central carrier;
   a guide wire catheter extending through the longitudinal lumen having a distal end and a proximal end;
   a nose cone dilator attached to and positioned at the proximal end of the guide wire catheter, the nose cone dilator having one or more apertures extending longitudinally therein;
   a capsule having a passageway extending therein with a distal closed end attached to the tubular carrier and an opening proximal end facing the nose cone dilator,
   the capsule being axially moveable along the guide wire catheter with respect to the nose cone dilator;
   a stent graft having a distal end and a proximal end positioned distal to the nose cone dilator; and,
   a first retention arrangement on the guide wire catheter for the proximal end of the stent graft, the first retention arrangement being distal to the nose cone dilator;
   wherein the system having a curved proximal end and having a radius of curvature of from 70 to 150 mm for approximating the thoracic aortic arch of the patient so as not to put excessive load on a wall of the thoracic aortic arch when positioned therein, and
   wherein the delivery system further comprises one or more proximal trigger wires extending longitudinally along the tubular carrier and independently extendable into the one or more apertures of the nose cone dilator.

2. A thoracic stent graft delivery system as in claim 1 wherein the proximal end of the guide wire catheter and the nose cone dilator together are curved to provide the proximal end of the system.

3. A thoracic stent graft delivery system as in claim 1 wherein the capsule provides a second retention arrangement on the tubular carrier for the distal end of a stent graft.

4. A thoracic stent graft delivery as in claim 3, wherein the second retention arrangement includes an aperture extending through the capsule and a distal trigger wire extending along the tubular carrier and extendable through the aperture.

5. A thoracic stent graft deployment apparatus for positioning a thoracic aorta stent graft into a thoracic aortic arch of a patient, the stent graft deployment apparatus comprising:
   a deployment catheter having a proximal end to be introduced into a patient and a distal end to remain outside a patient, the catheter having at a proximal end thereof a region in use to contain a stent graft;
   a sheath arrangement adapted in use to extend over and cover the region adapted to be moved with respect to the catheter to expose the region to thereby enable deployment of the stent graft;
   a nose cone dilator positioned at the proximal end of the deployment catheter, the nose cone dilator has one or more apertures extending longitudinally therein;
   a distal retention arrangement for the stent graft at a distal end of the region and comprising a capsule having a passageway extending therein with a distal closed end and an open proximal end facing the nose cone dilator; and,
   the nose cone dilator comprising a proximal end, wherein the proximal end of the nose cone dilator is curved, the curved proximal end comprising a radius of curvature of from 70 to 150 mm for approximating the thoracic aortic arch of the patient so as not to put excessive load on a wall of the thoracic aortic arch when positioned therein, and
   wherein the delivery system further comprises one or more proximal trigger wires extending longitudinally along the tubular carrier and independently extendable into the one or more apertures of the nose cone dilator.

6. A thoracic stent graft deployment apparatus as in claim 5 including a longitudinal lumen through the deployment catheter;
   a guide wire catheter extending through the longitudinal lumen and extending proximally of the deployment catheter, the guide wire catheter having a proximal end and a distal end;
   the guide wire catheter being moveable longitudinally and rotationally with respect to the deployment catheter; and,
   the nose cone dilator being attached to proximal end of the guide wire catheter and extending proximally thereof.

7. A thoracic stent graft deployment apparatus as in claim 6 including a proximal retention arrangement on the guidewire catheter distal of the nose cone dilator for the proximal end of the stent graft.

8. A thoracic stent graft deployment apparatus as in claim 5 wherein the one or more proximal trigger wires extend from the outside of the patient where it is retained by a proximal trigger wire release mechanism on a handle at the distal end of the deployment catheter.

9. A thoracic stent graft deployment apparatus as in claim 5 wherein the distal retention arrangement includes an aperture extending through the capsule and a distal trigger wire extending along the deployment catheter and extendable through the aperture.

10. A thoracic stent graft deployment apparatus as in claim 9 wherein the distal trigger wire extends from the outside of the patient where it is retained by a distal trigger wire release mechanism on a handle at the distal end of the deployment catheter.

11. A thoracic stent graft delivery system for positioning a thoracic aorta stent graft into a thoracic aortic arch of a patient, the delivery system comprising:
   a tubular central carrier having a distal end and a proximal end;
   a longitudinal lumen through the tubular central carrier;
   a guide wire catheter extending through the longitudinal lumen having a distal end and a proximal end;
   a nose cone dilator attached to and positioned at the proximal end of the guide wire catheter, the nose cone dilator has one or more apertures extending longitudinally therein; and;
   a capsule having a passageway extending therein with a distal closed end attached to the tubular carrier and an opening proximal end facing the nose cone dilator, the capsule being axially moveable along the guide wire catheter with respect to the nose cone dilator;
   wherein the nose cone dilator having a fixed curved for approximating the thoracic aortic arch of the patient so as not to put excessive load on a wall of the thoracic aortic arch when positioned therein, and
   wherein the delivery system further comprises one or more proximal trigger wires extending longitudinally along the tubular carrier and independently extendable into the one or more apertures of the nose cone dilator.

12. The thoracic stent graft delivery system of claim 11, further comprising a stent graft having a distal end and a proximal end positioned distal to the nose cone dilator, and a proximal retention arrangement on the guidewire catheter for the proximal end of the stent graft, the proximal retention arrangement being distal of the nose cone dilator.

* * * * *